(12) United States Patent
Weber (10) Patent No.: US 7,279,664 B2
(45) Date of Patent: Oct. 9, 2007

(54) RESONATOR FOR MEDICAL DEVICE

(75) Inventor: Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 11/189,526

(22) Filed: Jul. 26, 2005

(65) Prior Publication Data

US 2007/0023424 A1 Feb. 1, 2007

(51) Int. Cl.
*H05B 6/10* (2006.01)
*H61F 2/06* (2006.01)

(52) U.S. Cl. .................. 219/635; 623/1.1; 623/1.22

(58) Field of Classification Search ............... 219/635, 219/636, 637, 643; 623/1.1, 1.22, 1.15; H05B 6/10; A61F 2/06
See application file for complete search history.

(56) References Cited

U.S. PATENT DOCUMENTS

| | | | |
|---|---|---|---|
| 5,227,739 A * | 7/1993 | Mandai et al. ............... 331/96 |
| 5,409,460 A | 4/1995 | Krumme ...................... 604/107 |
| 5,824,045 A | 10/1998 | Alt ................................ 623/1 |
| 5,926,078 A * | 7/1999 | Hino et al. .................. 333/202 |
| 6,027,510 A | 2/2000 | Alt ............................. 606/108 |
| 6,053,873 A | 4/2000 | Govari et al. ............... 600/505 |
| 6,099,561 A | 8/2000 | Alt ............................ 623/1.44 |
| 6,106,473 A | 8/2000 | Violante et al. ............ 600/458 |
| 6,159,142 A | 12/2000 | Alt ................................ 600/3 |
| 6,159,237 A | 12/2000 | Alt et al. .................... 623/1.11 |
| 6,206,835 B1 | 3/2001 | Spillman et al. |
| 6,231,516 B1 | 5/2001 | Keilman et al. ............ 600/485 |
| 6,245,104 B1 | 6/2001 | Alt ............................ 623/1.46 |
| 6,251,134 B1 | 6/2001 | Alt et al. .................... 623/1.16 |
| 6,280,385 B1 | 8/2001 | Melzer et al. .............. 600/423 |
| 6,304,769 B1 | 10/2001 | Arenson et al. ............ 600/424 |
| 6,387,121 B1 | 5/2002 | Alt ............................ 623/1.15 |
| 6,398,805 B1 | 6/2002 | Alt ............................ 623/1.15 |
| 6,416,540 B1 | 7/2002 | Mathur ...................... 623/1.15 |
| 6,463,317 B1 | 10/2002 | Kucharczyk et al. ....... 600/411 |
| 6,478,815 B1 | 11/2002 | Alt ............................ 623/1.15 |
| 6,511,325 B1 | 1/2003 | Lalka et al. ................ 434/272 |

(Continued)

FOREIGN PATENT DOCUMENTS

DE 197 46 735 A1 4/1999

(Continued)

OTHER PUBLICATIONS

International Search Report, Dec. 8, 2006 (5 pgs).

*Primary Examiner*—Daniel Robinson
(74) *Attorney, Agent, or Firm*—Brooks, Cameron & Huebsch, PLLC (57) ABSTRACT

A resonator device including an induction coil, a conductive member positioned adjacent the induction coil, and a dielectric layer between at least a portion of the induction coil and the conductive member to form a capacitor structure. In one embodiment, the conductive member can be a stent. In an alterative embodiment, the conductive member can be a conductive film. In an additional embodiment, the dielectric layer can have a dielectric constant that changes in a predetermined fashion between at least a portion of the induction coil and the conductive member to allow for a uniform current distribution in the resonator device. The dielectric layer can also include a flexible elongate body.

14 Claims, 5 Drawing Sheets

U.S. PATENT DOCUMENTS

| | | |
|---|---|---|
| 6,516,213 B1 | 2/2003 | Nevo .......................... 600/424 |
| 6,574,497 B1 | 6/2003 | Pacetti ....................... 600/420 |
| 6,585,660 B2 | 7/2003 | Dorando et al. ............ 600/486 |
| 6,585,755 B2 | 7/2003 | Jackson et al. ............ 623/1.15 |
| 6,585,763 B1 | 7/2003 | Keilman et al. ........... 623/1.42 |
| 6,628,980 B2 | 9/2003 | Atalar et al. ............... 600/423 |
| 6,663,570 B2 | 12/2003 | Mott et al. .................. 600/486 |
| 6,676,694 B1 | 1/2004 | Weiss ......................... 623/1.11 |
| 6,702,847 B2 | 3/2004 | DiCarlo ..................... 623/1.34 |
| 6,711,429 B1 | 3/2004 | Gilboa et al. .............. 600/407 |
| 6,711,440 B2 | 3/2004 | Deal et al. ...................... 607/9 |
| 6,712,844 B2 | 3/2004 | Pacetti ....................... 623/1.15 |
| 6,716,237 B1 | 4/2004 | Alt ............................. 623/1.11 |
| 6,718,203 B2 | 4/2004 | Weiner et al. ................. 607/2 |
| 6,718,207 B2 | 4/2004 | Connelly ....................... 607/9 |
| 6,725,092 B2 | 4/2004 | MacDonald et al. .......... 607/2 |
| 6,731,979 B2 | 5/2004 | MacDonald .................... 607/9 |
| 6,757,566 B2 | 6/2004 | Weiner et al. .............. 607/116 |
| 6,760,628 B2 | 7/2004 | Weiner et al. .............. 607/122 |
| 6,763,268 B2 | 7/2004 | MacDonald et al. ........... 607/9 |
| 6,765,144 B1 | 7/2004 | Wang et al. .................. 174/36 |
| 6,767,360 B1 | 7/2004 | Alt et al. .................... 623/1.15 |
| 6,778,856 B2 | 8/2004 | Connelly et al. ............. 607/32 |
| 6,782,284 B1 | 8/2004 | Subramanyan et al. ...... 600/407 |
| 6,786,904 B2 | 9/2004 | Döscher et al. .............. 606/28 |
| 6,795,730 B2 | 9/2004 | Connelly et al. ............... 607/9 |
| 6,795,736 B2 | 9/2004 | Connelly et al. ............. 607/36 |
| 6,799,069 B2 | 9/2004 | Weiner et al. ................... 607/3 |
| 6,802,811 B1 | 10/2004 | Slepian ....................... 600/309 |
| 6,802,857 B1 | 10/2004 | Walsh et al. ............... 623/1.15 |
| 6,803,549 B2 * | 10/2004 | Yu .............................. 219/619 |
| 6,808,535 B1 | 10/2004 | Jordan ........................ 623/1.34 |
| 6,819,954 B2 | 11/2004 | Connelly ..................... 607/27 |
| 6,819,958 B2 | 11/2004 | Weiner et al. .............. 607/116 |
| 6,829,509 B1 | 12/2004 | MacDonald et al. ........ 607/119 |
| 6,844,492 B1 | 1/2005 | Wang et al. .................. 174/36 |
| 6,845,266 B2 | 1/2005 | Weiner et al. ................. 607/2 |
| 6,847,837 B1 | 1/2005 | Melzer et al. .............. 600/421 |
| 6,849,836 B2 * | 2/2005 | Yu .............................. 219/619 |
| 6,850,804 B2 | 2/2005 | Eggers et al. ............... 607/103 |
| 6,850,805 B2 | 2/2005 | Connelly et al. ........... 607/122 |
| 6,875,180 B2 | 4/2005 | Weiner et al. .............. 600/508 |
| 6,884,234 B2 | 4/2005 | Aita et al. ............. 604/103.01 |
| 6,892,090 B2 | 5/2005 | Verard et al. .............. 600/424 |
| 6,898,454 B2 | 5/2005 | Atalar et al. ............... 600/410 |
| 6,901,290 B2 | 5/2005 | Foster et al. .................... 607/9 |
| 6,908,468 B2 | 6/2005 | Daum ........................... 606/76 |
| 6,925,322 B2 | 8/2005 | Helfer et al. ............... 600/423 |
| 6,925,328 B2 | 8/2005 | Foster et al. .................... 607/9 |
| 6,954,674 B2 | 10/2005 | Connelly ..................... 607/63 |
| 6,957,098 B1 | 10/2005 | Hyde et al. ................. 600/424 |
| 2001/0031919 A1 | 10/2001 | Strommer et al. .......... 600/424 |
| 2001/0031920 A1 | 10/2001 | Kaufman et al. ........... 600/431 |
| 2002/0019660 A1 | 2/2002 | Gianotti et al. ............ 623/1.15 |
| 2002/0026230 A1 | 2/2002 | Moll et al. .................. 623/1.13 |
| 2002/0040815 A1 | 4/2002 | Van Vaals ................... 600/411 |
| 2002/0045816 A1 | 4/2002 | Atalar et al. ............... 600/423 |
| 2002/0049375 A1 | 4/2002 | Strommer et al. .......... 600/407 |
| 2002/0082679 A1 | 6/2002 | Sirhan et al. ............... 623/1.15 |
| 2002/0082685 A1 | 6/2002 | Sirhan et al. ............... 623/1.42 |
| 2002/0137014 A1 | 9/2002 | Anderson et al. ........... 434/262 |
| 2002/0188345 A1 | 12/2002 | Pacetti ....................... 623/1.15 |
| 2003/0004562 A1 | 1/2003 | DiCarlo ..................... 623/1.13 |
| 2003/0004563 A1 | 1/2003 | Jackson et al. ............ 623/1.15 |
| 2003/0074049 A1 | 4/2003 | Hoganson et al. .......... 623/1.13 |
| 2003/0083579 A1 | 5/2003 | Aita et al. ................... 600/470 |
| 2003/0087244 A1 | 5/2003 | McCarthy ...................... 435/6 |
| 2003/0088178 A1 | 5/2003 | Owens et al. ............... 600/420 |
| 2003/0088308 A1 | 5/2003 | Scheuermann et al. .... 623/1.15 |
| 2003/0092013 A1 | 5/2003 | McCarthy et al. ............. 435/6 |
| 2003/0105069 A1 | 6/2003 | Robinson et al. ........... 514/185 |
| 2003/0139739 A1 | 7/2003 | Doscher et al. .............. 606/28 |
| 2003/0143544 A1 | 7/2003 | McCarthy ...................... 435/6 |
| 2003/0144728 A1 | 7/2003 | Scheuermann et al. .... 623/1.15 |
| 2003/0163052 A1 | 8/2003 | Mott et al. .................. 600/486 |
| 2003/0187335 A1 | 10/2003 | McCarthy ................... 600/300 |
| 2003/0199747 A1 | 10/2003 | Michlitsch et al. ......... 600/407 |
| 2003/0212448 A1 | 11/2003 | Smith ......................... 623/1.13 |
| 2004/0010304 A1 | 1/2004 | Weber et al. ............... 623/1.11 |
| 2004/0019376 A1 | 1/2004 | Alt ............................. 623/1.42 |
| 2004/0030379 A1 | 2/2004 | Hamm et al. ............... 623/1.15 |
| 2004/0034300 A1 | 2/2004 | Verard et al. .............. 600/424 |
| 2004/0038406 A1 | 2/2004 | Unger et al. ................ 435/459 |
| 2004/0039438 A1 | 2/2004 | Alt ............................. 623/1.15 |
| 2004/0044397 A1 | 3/2004 | Stinson ...................... 623/1.15 |
| 2004/0059280 A1 | 3/2004 | Makower et al. .............. 604/8 |
| 2004/0082866 A1 | 4/2004 | Mott et al. .................. 600/486 |
| 2004/0091603 A1 | 5/2004 | Priewe ...................... 427/2.24 |
| 2004/0093075 A1 | 5/2004 | Kuehne ...................... 623/1.15 |
| 2004/0097804 A1 | 5/2004 | Sobe .......................... 600/424 |
| 2004/0097805 A1 | 5/2004 | Verard et al. .............. 600/428 |
| 2004/0098093 A1 | 5/2004 | DiCarlo ..................... 623/1.13 |
| 2004/0117007 A1 | 6/2004 | Whitbourne et al. ....... 623/1.42 |
| 2004/0122494 A1 | 6/2004 | Eggers et al. ............... 607/103 |
| 2004/0143180 A1 | 7/2004 | Zhong et al. ............... 600/410 |
| 2004/0158310 A1 | 8/2004 | Weber et al. ............... 623/1.15 |
| 2004/0186377 A1 | 9/2004 | Zhong et al. ............... 600/431 |
| 2004/0210289 A1 | 10/2004 | Wang et al. ................ 607/116 |
| 2004/0230271 A1 | 11/2004 | Wang et al. ................ 607/116 |
| 2004/0243220 A1 | 12/2004 | Gianotti et al. ............ 623/1.15 |
| 2004/0249428 A1 | 12/2004 | Wang et al. ................ 607/116 |
| 2004/0254419 A1 | 12/2004 | Wang et al. .................... 600/8 |
| 2004/0254632 A1 | 12/2004 | Alt et al. .................... 623/1.15 |
| 2005/0004653 A1 | 1/2005 | Gerberding et al. ........ 623/1.13 |
| 2005/0025797 A1 | 2/2005 | Wang et al. ................ 424/422 |
| 2005/0033407 A1 | 2/2005 | Weber et al. ............... 623/1.15 |
| 2005/0049480 A1 | 3/2005 | Gray .......................... 600/407 |
| 2005/0049481 A1 | 3/2005 | Gray et al. ................. 600/407 |
| 2005/0049482 A1 | 3/2005 | Gray et al. ................. 600/407 |
| 2005/0049683 A1 | 3/2005 | Gray et al. ................. 623/1.15 |
| 2005/0049684 A1 | 3/2005 | Gray et al. ................. 623/1.15 |
| 2005/0049685 A1 | 3/2005 | Gray et al. ................. 623/1.15 |
| 2005/0049686 A1 | 3/2005 | Gray et al. ................. 623/1.15 |
| 2005/0049688 A1 | 3/2005 | Gray et al. ................. 623/1.16 |
| 2005/0049689 A1 | 3/2005 | Gray et al. ................. 623/1.16 |
| 2005/0065430 A1 | 3/2005 | Wiethoff et al. ........... 600/413 |
| 2005/0065437 A1 | 3/2005 | Weber et al. ............... 600/431 |
| 2005/0079132 A1 | 4/2005 | Wang et al. ................ 424/1.11 |
| 2005/0080459 A1 | 4/2005 | Jacobson et al. ............... 607/9 |
| 2005/0085895 A1 | 4/2005 | Brown et al. .............. 623/1.15 |
| 2005/0090886 A1 | 4/2005 | MacDonald et al. ........ 607/122 |
| 2005/0107870 A1 | 5/2005 | Wang et al. ................ 623/1.44 |
| 2005/0113669 A1 | 5/2005 | Helfer et al. ............... 600/412 |
| 2005/0113676 A1 | 5/2005 | Weiner et al. .............. 600/421 |
| 2005/0113873 A1 | 5/2005 | Weiner et al. ................. 607/2 |
| 2005/0113874 A1 | 5/2005 | Connelly et al. ............... 607/2 |
| 2005/0113876 A1 | 5/2005 | Weiner et al. ............... 607/36 |
| 2005/0131522 A1 | 6/2005 | Stinson et al. ............. 623/1.15 |
| 2005/0143651 A1 | 6/2005 | Verard et al. .............. 600/424 |
| 2005/0149002 A1 | 7/2005 | Wang et al ..................... 606/1 |
| 2005/0149157 A1 | 7/2005 | Hunter et al. .............. 607/119 |
| 2005/0149169 A1 | 7/2005 | Wang et al. ................ 623/1.15 |
| 2005/0152946 A1 | 7/2005 | Hunter et al. .............. 424/423 |
| 2005/0154374 A1 | 7/2005 | Hunter et al. ............ 604/890.1 |
| 2005/0155779 A1 | 7/2005 | Wang et al. .................. 174/35 |
| 2005/0158356 A1 | 7/2005 | Hunter et al. .............. 424/423 |
| 2005/0159661 A1 | 7/2005 | Connelly et al. ........... 600/410 |
| 2005/0165470 A1 | 7/2005 | Weber ........................ 623/1.15 |
| 2005/0165471 A1 | 7/2005 | Wang et al. ................ 623/1.15 |
| 2005/0169960 A1 | 8/2005 | Hunter et al. .............. 424/423 |
| 2005/0169961 A1 | 8/2005 | Hunter et al. .............. 424/423 |
| 2005/0175664 A1 | 8/2005 | Hunter et al. .............. 424/423 |
| 2005/0175665 A1 | 8/2005 | Hunter et al. .............. 424/423 |
| 2005/0175703 A1 | 8/2005 | Hunter et al. .............. 424/486 |

| | | | | | | | |
|---|---|---|---|---|---|---|---|
| 2005/0178395 A1 | 8/2005 | Hunter et al. | 128/898 | 2005/0192647 A1 | 9/2005 | Hunter et al. | 607/57 |
| 2005/0178396 A1 | 8/2005 | Hunter et al. | 128/898 | 2005/0196421 A1 | 9/2005 | Hunter et al. | 424/423 |
| 2005/0178584 A1 | 8/2005 | Wang et al. | 174/256 | 2005/0208095 A1 | 9/2005 | Hunter et al. | 424/423 |
| 2005/0181005 A1 | 8/2005 | Hunter et al. | 424/422 | 2005/0209664 A1 | 9/2005 | Hunter et al. | 607/115 |
| 2005/0181009 A1 | 8/2005 | Hunter et al. | 424/423 | 2005/0209665 A1 | 9/2005 | Hunter et al. | 607/115 |
| 2005/0181010 A1 | 8/2005 | Hunter et al. | 424/423 | 2005/0209666 A1 | 9/2005 | Hunter et al. | 607/115 |
| 2005/0182450 A1 | 8/2005 | Hunter et al. | 607/36 | 2005/0215764 A1 | 9/2005 | Tuszynski et al. | 530/358 |
| 2005/0182463 A1 | 8/2005 | Hunter et al. | 607/115 | 2005/0216075 A1 | 9/2005 | Wang et al. | 623/1.15 |
| 2005/0182467 A1 | 8/2005 | Hunter et al. | 607/116 | | | | |
| 2005/0182468 A1 | 8/2005 | Hunter et al. | 607/116 | | | | |
| 2005/0182469 A1 | 8/2005 | Hunter et al. | 607/116 | | | | |
| 2005/0183731 A1 | 8/2005 | Hunter et al. | 128/898 | | | | |
| 2005/0186239 A1 | 8/2005 | Hunter et al. | 424/422 | | | | |
| 2005/0186244 A1 | 8/2005 | Hunter et al. | 424/423 | | | | |
| 2005/0186245 A1 | 8/2005 | Hunter et al. | 424/423 | | | | |
| 2005/0187140 A1 | 8/2005 | Hunter et al. | 514/2 | | | | |
| 2005/0187582 A1 | 8/2005 | Weiner | 607/4 | | | | |
| 2005/0187600 A1 | 8/2005 | Hunter et al. | 607/115 | | | | |

FOREIGN PATENT DOCUMENTS

| | | |
|---|---|---|
| WO | WO99/42039 | 8/1999 |
| WO | WO99/42176 | 8/1999 |
| WO | WO 01/74241 | 10/2001 |
| WO | WO 02/30331 A1 | 4/2002 |
| WO | WO 02/094339 | 11/2002 |
| WO | WO 2005/037143 A1 | 4/2005 |

* cited by examiner

RESONATOR FOR MEDICAL DEVICE

FIELD OF THE INVENTION

The present invention relates generally to medical device apparatus, systems, and methods; and more particularly to medical device apparatus, systems, and methods for use during magnetic resonance imaging.

BACKGROUND

Stents and other metallic implants can cause artifacts in magnetic resonance (MR) images due in part to distortions in the magnetic field. Distortions in the magnetic field are often caused by the shape of the stent that acts to partially shield a radio frequency (RF) field generated during the MR procedure. This shielding of the RF field is known as the Faraday Effect and is caused by structures, such as stents, that have a "Faraday Cage" configuration.

Generally, a Faraday Cage configuration prevents an RF field from penetrating to the interior of such a structure. Because stents are not ideal but only partial Faraday cages, a small percentage of the RF field still is able to penetrate to the interior, however not enough to give a reasonable visibility in the stent interior.

One approach to achieving the reasonable visibility would be to raise the energy of the RF field to such high levels that enough energy remains after passing through the partial stent shield for visualization. Unfortunately, taking this approach will cause the tissue of the body to be heated to unacceptable levels.

BRIEF DESCRIPTION OF THE DRAWINGS

The illustrations provided in the Figures are not to scale.

DETAILED DESCRIPTION

The figures herein follow a numbering convention in which the first digit or digits correspond to the drawing figure number and the remaining two (2) digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments. In addition, discussion of features and/or attributes for an element with respect to one figure can also apply to the element shown in one or more additional figures.

Embodiments of the present invention are directed to medical device apparatus, systems, and methods of using the medical device. Generally, the medical device includes a resonator to be used in conjunction with an additional implantable medical device. These implantable medical devices include devices that traditionally have produced artifacts (signal loss) in images obtained by magnetic resonance imaging (MRI) systems. Embodiments of the present invention address the problem of artifacts (signal loss) produced in magnetic resonance (MR) images in addition to allowing for more complete MR images to possibly be obtained from implantable medical devices.

Examples of such implantable medical devices include, but are not limited to, stents and/or shunts as are used in dialysis, artificial veins, arteries and grafts, esophageal stenosis, esophageal cancer, esophageal varacies, lung bronchi for cancer treatment, urethra, hydrocephalus shunt elongate tubes, trachea, middle ear elongate tubes, lymphatic ducts and grafts, gastrointestinal stenosis and inflammatory diseases (e.g. Crohn's disease), pyloric stenosis, implantable sensing devices, intravascular blood pressure devices, and biliary atresia. Examples of other types of implantable medical devices are also possible.

Typically, artifacts in MR images are due in large part to distortions in the magnetic field caused by the implanted medical device. For example, metallic stents can cause susceptibility and radio frequency artifacts in MR images that do not allow for complete visualization of the stent lumen by magnetic resonance angiography (MRA). This is due to susceptibility artifacts and radio frequency shielding of the metallic stents. Embodiments of the present invention can provide the potential for reduced artifacts during MR imaging with different MRA techniques through the use of a resonator device in conjunction with a medical device (e.g., metallic vascular stent).

In addition to allowing for more complete MR images to be obtained from implantable medical devices, embodiments of the present invention can also allow for a more uniform amplification of a radio frequency (RF) magnetic field. An example of such an RF magnetic field includes those produced and sensed by during MRA. Providing a more uniform amplification of an RF magnetic field in and/or around an implanted medical device, such as a metallic stent, may allow for the resulting MR images from within the implanted medical device to provide more detailed and meaningful MR images.

Figure 1:
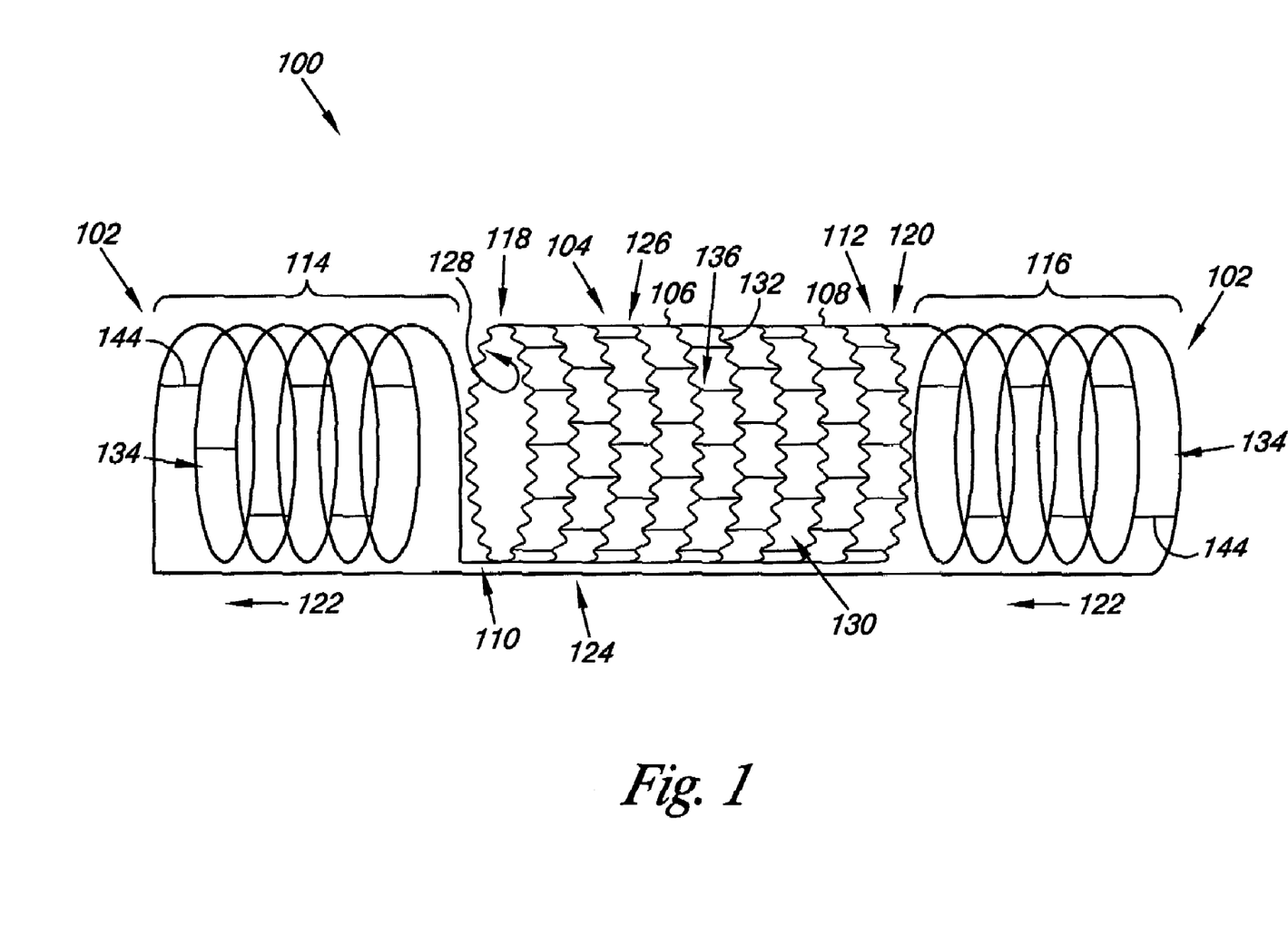
FIG. 1 illustrates an embodiment of a resonator device according to the present invention.

FIG. 1 illustrates one embodiment of a resonator device 100 of the present invention. The resonator device 100 is illustrated as having an induction coil 102 and a conductive member 104 positioned adjacent each other. In the present embodiment, the conductive member 104 is in the form of a vascular stent 106 that has an electrically conductive body. The resonator device 100 further includes a dielectric layer positioned between at least a portion of the induction coil 102 and the conductive member 104 to form a capacitor structure 108. The induction coil 102 can be electrically connected in series to the capacitor structure 108 to form the resonator device 100.

In various embodiments, the induction coil 102 can have a number of configurations that are positioned at a variety of locations relative the vascular stent 106. For example, as illustrated the induction coil 102 can include a first end 110 and a second end 112. The induction coil 102 can also include a first coil segment 114 and a second coil segment 116. As illustrated, the first coil segment 114 can be positioned adjacent a first stent end 118, and the second coil segment 116 can be positioned adjacent a second stent end 120. In one embodiment, the first coil segment 114 includes the first end 110 that is coupled to the electrically conductive body of the vascular stent 106. In an additional embodiment, the second coil segment 116 includes the second end 112 that is coupled in series through the dielectric layer to form the capacitor structure 108 of the resonator device 100.

In one embodiment, the windings of the first and second coil segments 114, 116 are wound in a common direction 122. In addition, the first and second coil segments 114, 116 are at least electrically coupled through the use of a connection member 124. As used herein, a winding includes an electrically conductive wire wound one complete turn about a center of the resonator device 100. In one embodiment, the connection member 124 can extend over the vascular stent 106 either adjacent an exterior surface 126 or an interior surface 128 of the vascular stent 106. In an alternative embodiment, the connection member 124 can be woven in and out of the vascular stent 106 structure.

In one embodiment, the connection member 124 can be constructed of the same material as the induction coil 102. Alternatively, the connection member 124 can be constructed of a material that is different (e.g., different conductivity, flexibility, malleability, stiffness) than the material used for the induction coil 102. In addition, the connection member 124 can have a number of different cross-sectional profiles, including but not limited to, circular, oval, triangular, and polygonal. The cross-sectional area of the connection member 124 can also be greater than or equal to that of the induction coil 102. For example, the connection member 124 could have a diameter that is greater than or equal to the diameter of the induction coil 102. In an alternative embodiment, the cross-sectional area of the connection member 124 can be less than or equal to that of the induction coil 102.

As illustrated, the connection member 124 can be an elongate member that passes adjacent the exterior surface 126 of the vascular stent 106. In an alternative embodiment, the connection member 124 can be in the form of a helix that extends along the resonator device 100. The connection member 124 can also be sheathed with an electrical insulator (e.g., e-PTFE or pyrolene) to electrically insulate the induction coil 102 from the vascular stent 106 and or the induction coil 102. In addition, one or more portions of the connection member 124 could be made radioopaque, as discussed herein.

In various embodiments, the vascular stent 106, the first coil segment 114 and the connection member 124 can be formed from a single piece of material. For example, the vascular stent 106, the first coil segment 114, and the connection member 124 could be cut (laser or water cut) from a single elongate tube of material. Alternatively, the vascular stent 106, the first coil segment 114 and the connection member 124 could be formed from a single length of material (e.g., a length of wire). The connection member 124 could then be connected to the second coil segment 116 of the induction coil 102. In one embodiment, connecting the connection member 124 to the second coil segment 116 can be accomplished through a welding process, such as laser welding.

In an alternative embodiment, the vascular stent 106, the first and second coil segments 114, 116 and the connection member 124 can be formed from either a single piece of material or a single length of material, as discussed herein. For example, in one configuration a single piece or length of material can be used to form, in order, the vascular stent 106, the first coil segment 114, the connection member 124 and the second coil segment 116. From this configuration, the connection member 124 would then be bent back over the windings of the first coil segment 110 to position the second coil segment 116 adjacent the second stent end 120. The second end 112 of the induction coil 102 can then be coupled through the dielectric layer to complete the circuit of the resonator device 100.

As illustrated in the present embodiment, the conductive member 104 is in the form of the vascular stent 106. The vascular stent 106 includes a tubular shaped body 130 defined by elongate members 132 disposed between the first and second end 118 and 120. The tubular shaped body 130 also includes a surface defining at least a portion of a lumen 134 of the resonator device 100. In one embodiment, the elongate member 132 can be formed of a material which is electrically conductive. In addition, the material of the elongate member 132 also has the requisite strength and elasticity characteristics to permit the tubular shaped body 130 to be expanded from the first cross-sectional size to the second cross-sectional size. The material also allows the tubular shaped body 130 to retain its expanded configuration with the second cross-sectional size. Examples of such materials include, but are not limited to, tantalum, magnesium, tungsten, niobium, stainless steel, titanium, memory metal alloys (such as Nitinol), or any suitable plastic material having the requisite characteristics described herein.

The elongate member 132 can have a cylindrical cross-section, but as will be appreciated the elongate member 132 could have other cross-sectional configurations, such as triangular, square, rectangular, and/or hexagonal, among others. In addition, the elongate member 132 can have a non-uniform cross-sectional configuration along its length, such as tapered, bell shaped, or changing from one cross-sectional shape (e.g., cylindrical) to a second cross-sectional shape (e.g., elliptical) in case of a bifurcation. As illustrated, the elongate member 132 can be configured as a continuous helix of connected spirals or loops having a sinuous or zigzag configuration. The elongate member 132 can also be fixedly secured to one another at predetermined intersection points and connectors 136 so as to help resist radial collapse of the vascular stent 106 and to help maintain its second cross-sectional size.

In the embodiment illustrated in FIG. 1, the vascular stent 106 is configured to function as the capacitor structure 108. In various embodiments, the vascular stent 106 has a layered configuration of the conductive member 104, a dielectric layer, and at least a portion of the induction coil 102 that forms the capacitor structure 108. For example, in the present embodiment the elongate member 132 forming the vascular stent 106 provides the conductive member 104. The dielectric layer is positioned over at least a portion of the elongate member 132, where the induction coil 102 is electrically connected in series to form the resonator device 100.

In one embodiment, the elongate member 132 and the portion of the induction coil 102 contacting the dielectric material form electrically isolated (insulated) conductive surfaces for the capacitor structure 108. In an additional embodiment, at least a portion of the elongate member 132 can further include an electrically conductive coating over the dielectric layer so as to increase the surface area of the capacitor structure 108. In other words, the capacitor structure 108 can include the elongate member 132 coated with the dielectric material, where the electrically conductive coating is provided over the dielectric to provide the capacitor structure 108. The second end 112 of the induction coil 102 can then be electrically coupled to the electrically conductive coating to complete the circuit of the resonator device 100. The capacitor structure 108 and/or the induction coil 102 can also be coated with an electrical insulator (e.g., e-PTFE or pyrolene) to electrically insulate the capacitor structure 108 and/or the induction coil 102.

Figure 2:
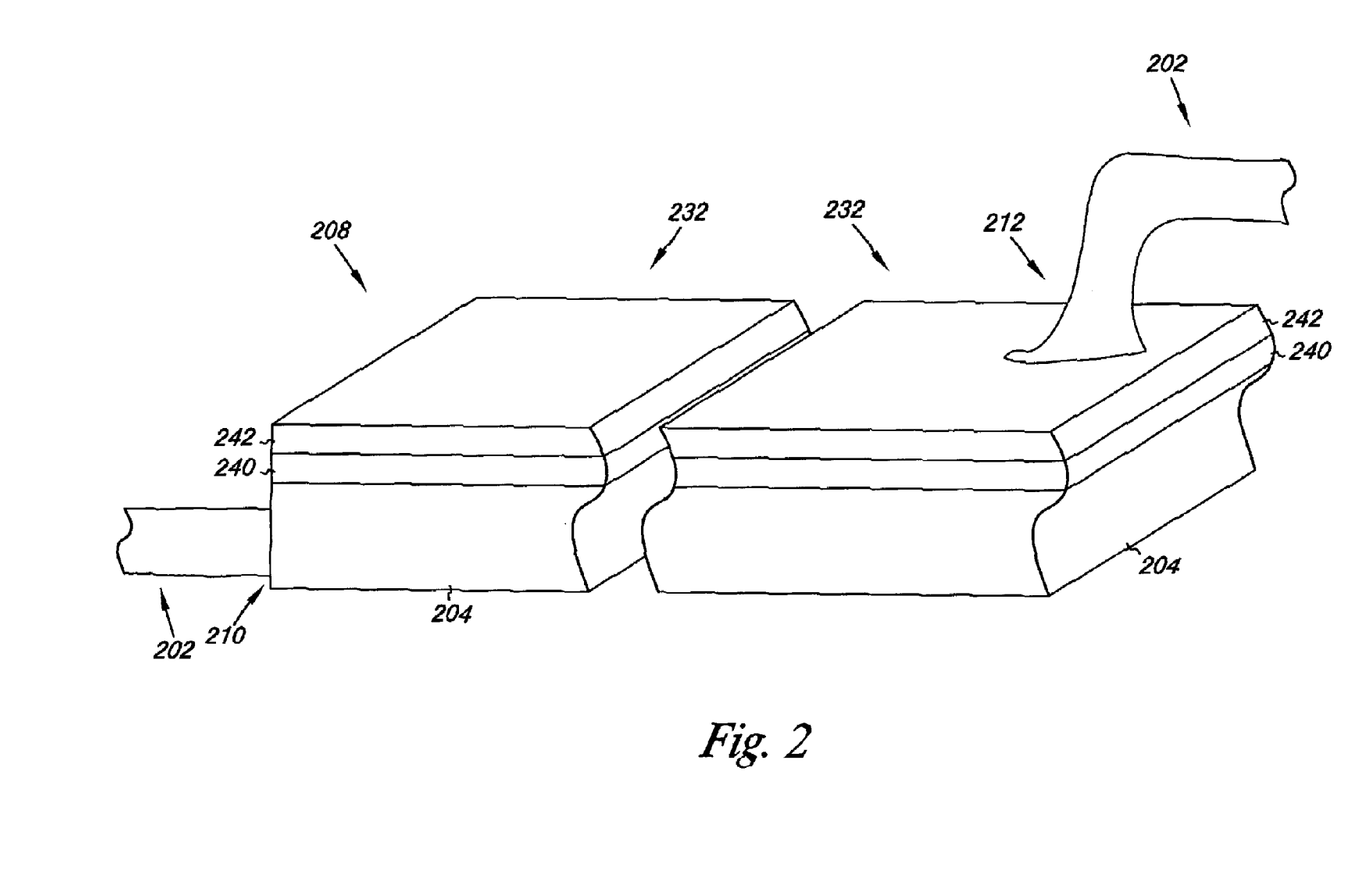
FIG. 2 illustrates an embodiment of a layered structure for a capacitor structure according to the present invention.

FIG. 2 provides an embodiment illustrating the layered structure of the capacitor structure described herein. As illustrated, the capacitor structure includes the elongate member 232 of the vascular stent that provides the conductive member 204. The dielectric layer 240 can be positioned over at least a portion of the elongate member 232. The electrically conductive coating 242 can then be positioned over the dielectric layer 240 to form the capacitor structure 208.

FIG. 2 also illustrates an embodiment of the capacitor structure 208. For example, the elongate member 232 coated with the dielectric material 240 and the electrically conductive coating 242 provides the capacitor structure 208. The first end 210 of the induction coil 202 can be electrically connected to the conductive member 204 and the second end 212 of the induction coil 202 can be electrically coupled to the electrically conductive coating 242 to complete the capacitor structure 208 of the resonator device.

Possible dielectric materials include, but are not limited to, metal oxides such as tantalum oxide, aluminum oxide, niobium oxide, niobium-zirconium alloy oxide; ceramic and/or glasses such as alumina or aluminosilicates and borosilicate; minerals such as mica (an alkali metal aluminosilicate, hydrate); polymers such as polyesters (e.g., Mylar), polyamides (e.g., Nylon), polycarbonate, polyetheretherketones (PEEK), poly(phenylene oxide), poly(phenylene sulfide), poly(vinyl chloride), poly(chlorotrifluoroethylene), poly(p-phenyleneethylene), polystyrene, polyethylene, polypropylene, and poly(tetrafluoroethylene). Other dielectric materials are also possible.

As will be appreciated, the dielectric layer and/or the electrically conductive coating can be formed as a film deposited on the elongate member 132 through a number of different surface coating techniques. Examples of such coating techniques include, but are not limited to, chemical or physical deposition techniques. Example of these respective techniques include, but are not limited to, solution casting, ink-jet deposition, aerosol deposition, dip coating, spin coating, plasma polymerization, electrochemical polymerization, catalytic polymerization, photo-activatable polymerization, molecular-aggregation, vacuum sublimation, plasma deposition, pulse-laser deposition (PLD), matrix assisted pulsed-laser evaporation, chemical vapor deposition (CVD), plasma assisted CVD, thin film growth, sputtering, evaporation (thermal and e-beam), ion vapor deposition, and laser and/or electron beam assisted processing (e.g., laser ablation processing).

In one embodiment, the dielectric layer of the capacitor structure 108 can have a dielectric constant that changes in a predetermined fashion between at least a portion of the induction coil 102 and the conductive member 104. In the various embodiments, configuring the changes in the dielectric constant along the capacitor structure 108 can allow for a more uniform current distribution to result in the resonator device 100.

Examples of such configurations include, but are not limited to, the dielectric layer having two or more sections that each has a dielectric constant that is different than the dielectric constant of other sections of the dielectric layer. This configuration can provide for a change in the capacitance value of the capacitor structure 108 between the first end 110 and the second end 112 of the induction coil 102. For example, the value of the dielectric constant for the two or more sections can increase between the first end 110 and the second end 112 of the induction coil 102 to change the capacitance value of the capacitor structure 108. In an additional embodiment, the dielectric layer can have a thickness that increases along the conductive member 104 of the vascular stent 106 between the first end 110 and the second end 112 of the induction coil 102 to change the capacitance value of the capacitor structure 108.

As illustrated in the present embodiment, the induction coil 102 extends from the first end 118 to the second end 120 of the stent 106. In various embodiments, the induction coil 102 can be configured to extend over at least a portion of the exterior surface 126 of the vascular stent 106. For example, a portion of the induction coil 102 can extend over the exterior surface 126 of one or both of the first and/or second ends 118, 120 of the vascular stent 106. In an additional embodiment, a portion of the induction coil 102 can extend over the interior surface 128 of one or both of the first and/or second ends 118, 120 of the vascular stent 106. Different combinations are also possible (e.g., one portion of the induction coil 102 extends over the exterior surface 126 at the first end 118 while a second portion of the induction coil 102 extends over the interior surface 128 at the second end 120).

As illustrated, the induction coil 102 includes an elongate configuration having windings that extend circumferentially in a helical structure as illustrated. In one embodiment, windings of the helical structure can be equally spaced from each other. In an alternative embodiment, windings of the helical structure can have a predetermined non-consistent spacing relative to each other along the helical structure. In one embodiment, this non-consistent spacing can allow for differences in the winding density (number of windings per meter) along the length of the induction coil 102.

In one embodiment, the induction coil 102 can extend continuously down the length of the resonator device 100 (i.e., the induction coil 102 does not deviate along the length of the resonator device 100). Alternatively, the induction coil 102 can include a "zigzag" configuration as the induction coil 102 extends down the length of resonator device 100. As will be appreciated, other shapes and configurations that can act as an induction coil, besides helical coils, are also possible.

The induction coil 102 can be formed of one or more conductive members (e.g., two or more members in parallel). In addition, different cross-sectional geometries can be used for the induction coil 102. For example, the cross-sectional geometries can include circular rectangular, oval and/or polygonal, among others. Other shapes are also possible.

The conductive members of the induction coil 102 can also have a number of different sizes and structural configurations. For example, the conductive members can have a size and a shape sufficient to maintain a predetermined shape of the induction coil 102 in its deployed state. Alternatively, the size and the shape of each of the induction coil 102 can be supported by a structural support, as discussed in co-pending U.S. Patent Application entitled "Resonator for Medical Device", U.S. patent application Ser. No. 11/207,304, can be configured to maintain the predetermined shape of the induction coil 102 in its deployed state.

In one embodiment, the conductive members of the induction coil 102 can be a metal or metal alloy. Examples of such metals and metal alloys include, but are not limited to, platinum, titanium, niobium, and memory metals alloys such as Nitinol, titanium-palladium-nickel, nickel-titanium-copper, gold-cadmium, iron-zinc-copper-aluminum, titanium-niobium-aluminum, hafnium-titanium-nickel, iron-manganese-silicon, nickel-titanium, nickel-iron-zinc-aluminum, copper-aluminum-iron, titanium-niobium, zirconium-copper-zinc, and nickel-zirconium-titanium. Other metal and metal alloys are also possible. Further examples include polymeric wires provided with noble metal (e.g., gold) sputter coat, such as polyamide 12, polyethylene, and polycarbonate sputter coated with gold.

In addition, one or more of the components of the resonator device 100 can be made radioopaque. For example, one or more portions of the induction coil 102 could be clad with a radioopaque material to make the resonator device 100 radioopaque. Alternatively, one or more discrete radioopaque markers having a predetermined shape can be added to predetermined portions of the resonator device 100. Example of suitable materials for the radioopaque markers include, but are not limited to, copper, tungsten, gold, silver, platinum and alloys thereof.

The induction coil 102 can further include spacers 144 positioned between the windings of the induction coils 102. In one embodiment, the spacers 144 provide for electrical insulation, structural support, and structural spacing for adjacent windings of the coil 102. Spacers 144 can be coupled to the induction coil 102 in a number of ways. For example, a pair of spacers 144 could be sandwiched around the induction coil 102 and bonded with heat and/or chemical adhesive. Spacers 144 could be wound, twisted and/or braided around each other and the induction coil 102. The spacers 144 could then be bonded with heat and/or chemical adhesive.

Examples of suitable materials for the spacers 144 include, but are not limited to non-biodegradable and/or biodegradable materials. Examples of non-biodegradable materials include, but are not limited to, ceramic, polystyrene; polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL); squalene emulsions; and mixtures and copolymers of any of the foregoing.

Examples of biodegradable materials include, but are not limited to, polycarboxylic acid, polylactic acid, polyhydroxybuterate, polyanhydrides including maleic anhydride polymers; polyorthoesters; poly-amino acids; polyethylene oxide; polyphosphazenes; polyactic acid, polyglycolic acid and copolymers and copolymers and mixtures thereof such as poly(L-lactic acid) (PLLA), poly(D,L,-lactide), poly(lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocaronates, and polydimethyltrimethylcarbonates; cyanoacrylate; calcium phosphates; polyglycosaminoglycans; macromolecules such as polysaccharides (including hyaluronic acid, cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

The spacers 144 can further include one or more therapeutic agents. In one embodiment, the one or more therapeutic agents can be integrated into the material matrix of and/or coated on the surface of the spacers 144. The one or more therapeutic agents can then leach and/or be released from the spacers 144 once implanted.

Examples of therapeutic agents include, but are not limited to, pharmaceutically acceptable agents such as non-genetic therapeutic agents, a biomolecule, a small molecule, or cells. Exemplary non-genetic therapeutic agents include anti-thrombogenic agents such as heparin, heparin derivatives, prostaglandin (including micellar prostaglandin E1), urokinase, and PPack (dextrophyenylalanine proline arginine chloromethylketone); anti-proliferative agents such as enoxaprin, angiopenptin, sirolimus (rapamycin), tacrolimus, everolimus monoclonal antibodies capable of blocking smooth muscle cell proliferation, hirudin, and acetylsalicylic acid; anti-inflammatory agents such as dexamethasone, rosiglitazone, prenisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl)ethyleneglycol-N,N,N',N'-tetraacetic acid and mixtures thereof; antibiotics such as gentamycin rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vasoactive mechanisms; inhibitors of heat shock proteins such as geldanamycin; and any combinations and prodrugs of the above.

Exemplary biomolecules includes peptides, polypeptides and proteins; oligonucleotides; nucleic acids such as double or single stranded DNA (including naked and cDNA), RNA, antisense nucleic acids such as antisense DNA and RNA, small interfering RNA (siRNA), and riobozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedghog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-linear example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin-) cells including Lin-CD34−, Lin-CD34+, Lin-cKit+, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

The therapeutic agents may be combined to the extent such combination is biologically compatible.

The induction coil 102 and the vascular stent 106 are configured to allow the lumen 134 of the resonator device 100 to expand from a first cross-sectional size in an un-deployed state to a second cross-sectional size in a deployed state. This allows the resonator device 100 to be introduced into a body with the first cross-sectional size and then be expanded to the second cross-sectional size at the predetermined location within the body. For example, the resonator device 100 can be positioned over a balloon of a balloon catheter in its first cross-sectional size (e.g., its un-deployed configuration). The balloon can then be inflated to expand the resonator device 100 to its second cross-sectional size (e.g., its deployed configuration). Alternatively, when the induction coil 102 and vascular stent 106 are formed of a memory metal alloy (such as Nitinol), the resonator device 100 can be introduced into the body in its first cross-sectional size (e.g., its un-deployed configuration) and then released to expand the resonator device 100 to its second cross-sectional size (e.g., its deployed configuration).

In one embodiment, the diameter of lumen 134 can be essentially equal along the length of the resonator device 100. In an alternative embodiment, the expandable diameter of the lumen 134 can change along the length of the resonator device 100. For example, the diameter of the lumen 134 can increase or decrease along the length of the resonator device 100. Alternatively, the diameter of the lumen 134 can increase along the length of the resonator device 100 to a predetermined point and then decrease again. Other configurations are also possible.

As will be appreciated, the induction coil 102 includes windings of electrically conductive material that in conjunction with the capacitor structure 108 can be used to tune the resonator device 100 to a predetermined radio frequency (RF). Examples of parameters used in tuning the resonator device 100 include, but are not limited to, the number of windings and the cross sectional area of the induction coil 102. In one embodiment, the number of windings can be modified based on the configuration of induction coil 102. Parameters of the capacitor structure 108 can also be used in the tuning the resonator device 100.

Figure 3:
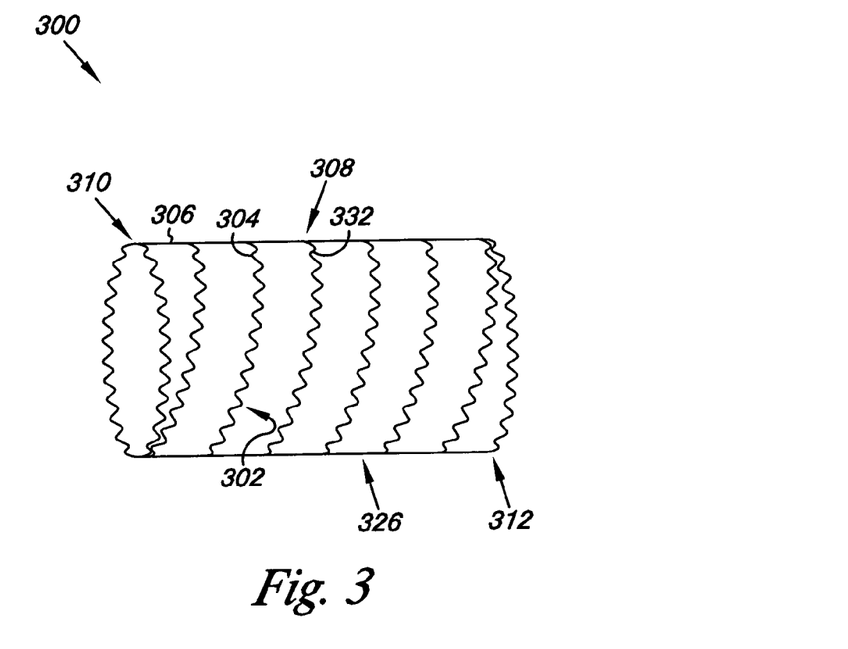
FIG. 3 illustrates an embodiment of a resonator device according to the present invention.

FIG. 3 illustrates an additional embodiment of the resonator device 300 of the present invention. As illustrated, the resonator device 300 is in the form of a vascular stent 306, as discussed generally herein. The resonator device 300 includes the elongate members 332 of the stent 306 that provide both the mechanical strength to support a vessel and the conduction member 304 for the capacitor structure 308. The resonator device 300 further includes both the induction coil 302 and the capacitor structure 308 that overly the conduction member 304 of the vascular stent 306 to form the resonator device 300. In other words, the resonator device 300 is integrated into the vascular stent 306. As discussed herein, the resulting resonator device 300 can resonate at the magnetic resonant frequency as used by the RF generator within the MRI system.

By way of example, the layers forming the induction coil 302 and the dielectric layer are located over predetermined portions of the conduction member 304 so as to provide the induction coil 302 and capacitor structure 308. In one embodiment, the layers forming the induction coil 302 and the capacitor structure 308 are applied to or formed upon the exterior surface 326 of the vascular stent 306. An example of such a structure is provided in U.S. Pat. No. 6,767,360 to Alt et al., which is incorporated herein by reference in its entirety.

As illustrated in FIG. 3, the induction coil 302 has a predetermined pattern on the exterior surface 326 of the vascular stent 306. The capacitor structure 308 can further be formed between the induction coil 302 and the elongate member 332 of the vascular stent 306. In one embodiment, this can be achieved by depositing (or otherwise creating) the dielectric layer on the exterior surface 326 of the vascular stent 306 in a circumferential pattern that extends along the vascular stent 306. In one embodiment, the circumferential pattern extending along the vascular stent 306 corresponds to the configuration of the induction coil 302. The electrically conductive material forming the induction coil 302 can then be deposited (or created) over the dielectric layer so as to complete the resonator circuit 300.

In one embodiment, the dielectric layer of the capacitor structure 308 can have a dielectric constant that changes, as discussed herein, in a predetermined fashion between at least a portion of the induction coil 302 and the conductive member 304. For example, the dielectric layer can include two or more sections that each has a dielectric constant that is different than the dielectric constant of other sections of the dielectric layer. This configuration can provide for a change in the capacitance value of the capacitor structure 308 between the first end 310 and the second end 312 of the induction coil 302, as discussed herein. In an additional embodiment, the dielectric layer can have a thickness that increases along the conductive member 304 of the vascular stent 306 between the first end 310 and the second end 312 of the induction coil 302 to change the capacitance value of the capacitor structure 308.

Figure 4:
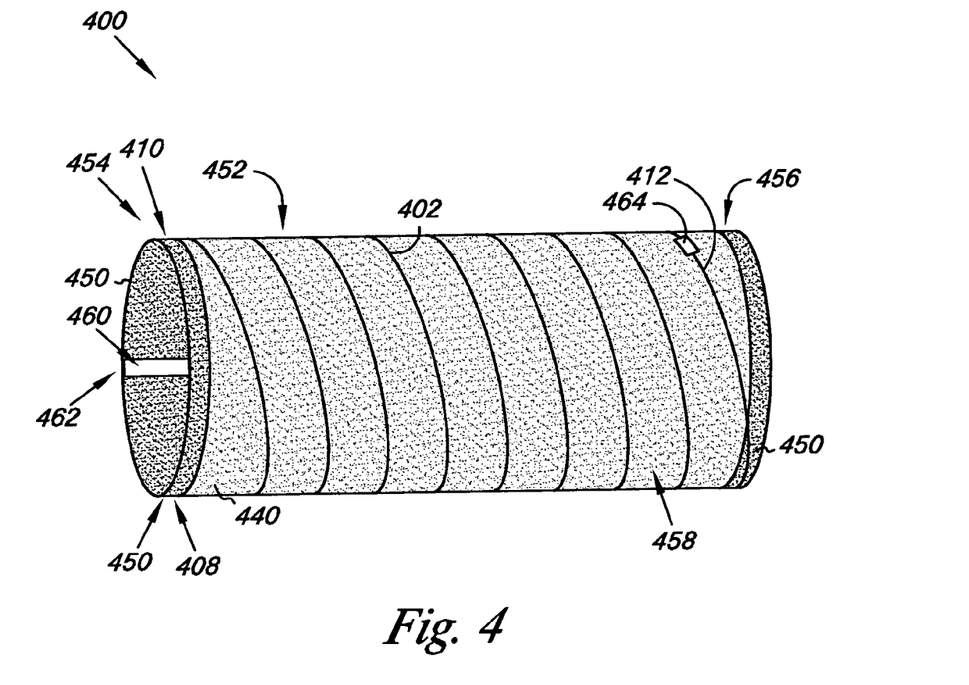
FIG. 4 illustrates an embodiment of a resonator device according to the present invention.

FIG. 4 provides an additional embodiment of the resonator device 400 that includes the induction coil 402, a conductive film 450 positioned adjacent the induction coil 402, and a dielectric layer 440. As illustrated, the dielectric layer 440 can be positioned between at least a portion of the induction coil 402 and the conductive film 450 to form the capacitor structure 408. As will be discussed herein, the dielectric layer 440 can be in the form of a flexible elongate body on which the induction coil 402 and conductive film 450 are positioned.

As illustrated in FIG. 4, the dielectric layer 440 is configured as an elongate tube 452 having a first end 454 and a second end 456. The elongate tube 452 includes a first surface 458 and a second surface 460 opposite the first surface 458. In one embodiment, the conductive film 450 can be located on at least a portion of the first surface 458 and the second surface 460. For example, the conductive film 450 on the second surface 460 can be at least partially contiguous with the conductive film 450 on the first surface 458 adjacent the first end 454, and the conductive film 450 on the second surface 460 can be separated from the conductive film 450 on the first surface 458 adjacent the second end 456.

As illustrated, the induction coil 402 can be located on the second surface 460 where the first end 410 of the induction coil 402 can be electrically coupled to the conductive film 450 adjacent the first end 454 of the elongate tube 452. The second end 412 of the induction coil 402 can be electrically coupled to the conductive film 450 adjacent the second end 456 of the elongate tube 452. In one embodiment, this allows for the elongate tube 452 to form the dielectric layer 440 to complete the circuit of the resonator device 400. In an additional embodiment, the resonator device 400 can further include a resistor 464 in series with the induction coil 402, the conductive film 450 and the capacitor structure 408. In one embodiment, use of the resistor 464 can allow for a wider frequency response of the resonator device 400 as compared to devices without such a resistor 464.

As illustrated, the conductive film 450 extends longitudinally along the first surface 458 of the elongate tube 450. In addition, the conductive film 450 defines a gap 462 that extends longitudinally along the first surface 458 of the elongate tube 452. In one embodiment the gap 462 provides for a break in the film 450 so as to prevent the conductive film 450 from interfering with received and amplified RF signals from the resonator device 400. As will be appreciated, changes in the surface area of film 450, and the induction coil 402, along with the choice of dielectric material can influence the operating parameters of the capacitor structure 408.

In one embodiment, the dielectric layer 440 configured as the elongate tube 452 can be formed by an extrusion process. Alternatively, the elongate tube 452 structure of the dielectric layer 440 can be formed by a weaving or knitting process using one or more filaments, or multi-filament yarn, of the dielectric material as described herein. Examples of suitable dielectric materials for use as the elongate tube 452 and/or use on the elongate tube 452 include, but are not limited to, those described herein. In addition, the elongate tube 452 can be formed, at least partially, of a biodegradable material, as are provided herein. As will be appreciated, the dielectric layer 440 may also be coated with one or more therapeutic agents, proteins, biomolecules, anticoagulant, anti-inflammatory, pro-endothelization compounds, among others, as described herein.

In one embodiment, the conductive film 450 and the induction coil 402 can be formed from an electrically conducive thin film as positioned on the elongate tube 452. Forming the conductive film 450 and the induction coil 402 as a thin conductive film can be accomplished in a number of ways. For example, the conductive film 450 and the induction coil 402 can be formed using either chemical or physical deposition techniques. Example of these techniques include, but are not limited to, chemical vapor deposition (CVD), plasma assisted CVD, thin film growth, sputtering, evaporation (thermal and e-beam), ion vapor deposition, and laser and/or electron beam assisted processing (e.g., laser ablation processing).

As will be appreciated, the conductive film 450 and the induction coil 402 can have a thickness sufficient to conduct the energy through the resonator device 400. In addition, the induction coil 402 and/or the conductive film 450 can be formed of conductive nanoparticles. As used herein, a nanoparticle is a microscopic particle whose size is measured in nanometers. Examples of suitable nanoparticles include those that can be oxidized, including but not limited to gold (Au). In one embodiment, this allows for the induction coil 402 and/or the conductive film 450 formed of the nanoparticles to be biodegradable.

In various embodiments, the conductive film 450 having the gap 462 can first be formed on the elongate tube 452, where the second surface 460 is initially defines the outside surface of the tube 452. In one embodiment, the conductive film 450 with the gap 462 is formed on the second surface 460 of elongate tube 452. As the conductive film 450 is formed a portion of the material forming the film covers the first and second end 454, 456 and a portion of the first surface 458 that initially defines the lumen of the tube 452. The wall of the tube 452 can then be inverted so that the first surface 458 defines the outside surface and the second surface 460 defines the lumen of the tube 452.

The induction coil 402 can then be formed on the first surface 458, where the first end 410 of the induction coil 402 can be electrically coupled to the conductive film 450 adjacent the first end 454 of the elongate tube 452. The second end 412 of the induction coil 402 can be electrically coupled to the conductive film 450 adjacent the second end 456 of the elongate tube 452. Conductive film 450 on the second end 456 can then be removed so as to allow the elongate tube 452 to form the dielectric layer 440 to complete the circuit of the resonator device 400.

As discussed herein, stents and other metallic implants can cause partial shielding of a RF field by the Faraday Effect. As a result, it has been difficult to obtain MRI visibility inside an implant. In an effort to obtain a better MRI visibility the implant can be positioned inside of the RF field of a local (implanted) resonating circuit, as discussed herein, that is tuned to the RF-frequency of the MRI system. The resonator-coil will cause the RF-field (as sent out by the MRI coil) to be magnified inside the coil. The result is to raise the energy level at the position of the implant without heating other parts of the body.

Embodiments of the resonator device 400 can be used in association, or in conjunction, with a vascular stent or other medical device. For example, the resonator device can be provided partially over at least a part of the vascular stent. In another example, the resonator device 400 can be provided partially within at least a part of the vascular stent. The resonator device 400 in conjunction with the vascular stent can then operate in the presence of an electromagnetic field produced by an MRI system to reduce the artifacting (signal loss) in images obtained by an MRI system.

Figure 5:
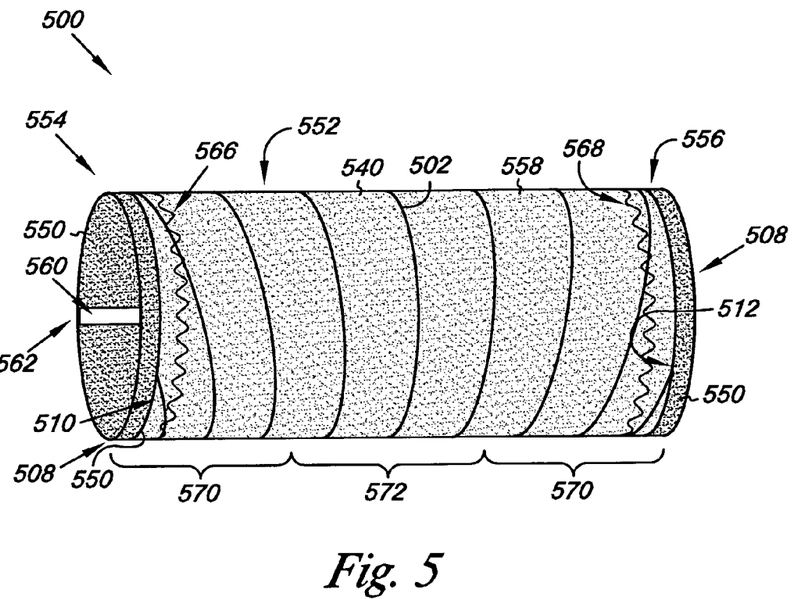
FIG. 5 illustrates an embodiment of a resonator device according to the present invention.

FIG. 5 provides an additional embodiment of the resonator device 500 that includes the induction coil 502, the conductive film 550 positioned adjacent the induction coil 502, and the dielectric layer 540. As illustrated, the dielectric layer 540 can be positioned between at least a portion of the induction coil 502 and the conductive film 550 to form the capacitor structure 508. As discussed herein, the dielectric layer 540 is in the form of the elongate tube 552 having the first end 554 and the second end 556.

The elongate tube 552 of the present embodiment further includes a first expandable support member 566 adjacent the first end 554 and a second expandable support member 568 adjacent the second end 556. In one embodiment, the first and second expandable support members 566, 568 are electrically isolated from the induction coil 502. As illustrated, the first and second expandable support members 566, 568 can at least partially encircle the elongate tube 552. In one embodiment, the first and second expandable support members 566, 568 can include one or more rings that fully encircle the elongate tube 552. In an alternative embodiment, the first and second expandable support members 566, 568 are partial rings that either do not fully encircle the elongate tube 552 or have a helical configuration in which each respective support member 566, 568 does not form a closed and connected loop (i.e., the first and second expandable support members 566, 568 have a first and a second end that are uncoupled).

The first and second expandable support members 566, 568 are configured to change shape from a first diameter that permits intraluminal delivery of the resonator device 500 into a body passageway, e.g., a lumen of the vasculature, to a second diameter that is larger than the first diameter. In one embodiment, the first and second expandable support members 566, 568 can have a sinuous or a zigzag pattern that encircles the elongate tube 552. As will be appreciated, this type of configuration allows the first and second expandable support members 566, 568 to be expanded from their first diameter to the second diameter.

The first and second expandable support members 566, 568 can be formed of a material which has the requisite strength and elasticity characteristics to permit the support members to be expanded from the first diameter to the second diameter. The material also allows the first and second expandable support members 566, 568 to retain their expanded configuration with the second diameter. Examples of such materials include, but are not limited to, tantalum, stainless steel, titanium, memory metal alloys (such as Nitinol), or any suitable plastic material having the requisite characteristics described herein.

In one embodiment, the first and second expandable support members 566, 568 help to secure the resonator device 500 at a predetermined position within a patient. For example, the resonator device 500 could be positioned upon a deflated balloon of a balloon catheter system. Upon positioning the resonator device 500 at a predetermined location within the patients, the resonator device 500 could be implanted by inflating the balloon to expand the first and second expandable support members 566, 568 so as to engage the resonator device 500 at the implant site. In an alternative embodiment, the first and second expandable support members 566, 568 can be self-expanding, where the catheter delivery system would constrain the first and second expandable support members 566, 568 in their first diameter until they were released at the implant site.

FIG. 5 also illustrates an additional embodiment for a configuration of the induction coil 502. As illustrated, the induction coil 502 includes a helical configuration with a pitch that transitions from a first predetermined value 570 to a second predetermined value 572 as the induction coil 502 extends longitudinally from the first end 510 of the induction coil 502. In one embodiment, the second predetermined value 572 occurs between the first end 510 and the second end 512 of the induction coil 502. In addition, the pitch of the induction coil 502 transitions from the second predetermined value 572 back to the first predetermined value 570 as the induction coil 502 extends longitudinally toward the second end 512 of the induction coil 502. In one embodiment, imparting the pitch to the induction coil 502 as illustrated and described herein can allow the resonator device 500 to receive and amplify RF signals impinging on the resonator device 500 from a greater variety of angles.

Figure 6:
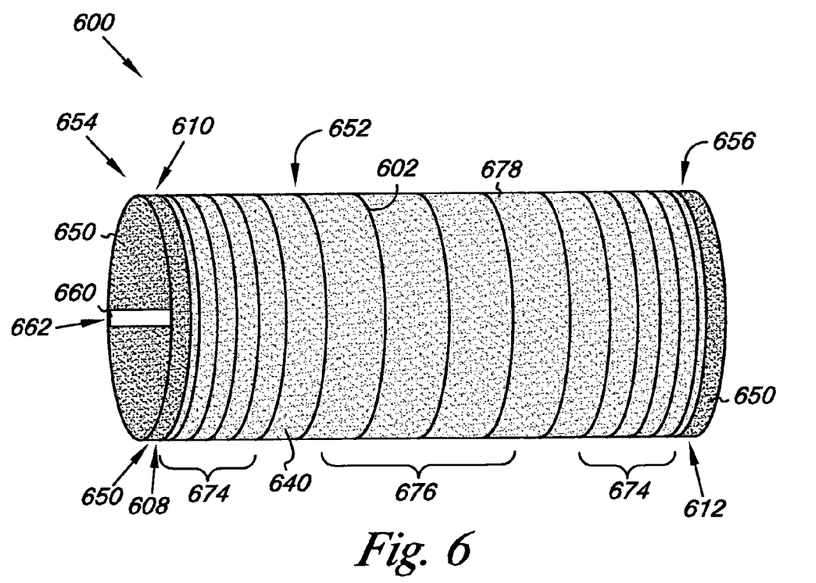
FIG. 6 illustrates an embodiment of a resonator device according to the present invention.

FIG. 6 provides an additional embodiment of the resonator device 600 for implanting in a body. The resonator device 600 includes the induction coil 602 having a first end 610 and a second end 612, as discussed herein. The resonator device 600 also includes a capacitor structure 608 in series with the induction coil 602, as discussed herein. As will be appreciated, other capacitor structures besides those described herein are also possible. Examples include plate capacitors and fractal capacitors.

In various embodiments, the induction coil 602 can further include a first density 674 and a second density of windings per meter for the induction coil 602 configured so as to allow for a uniform current distribution in the resonator device 600. For example, the induction coil 602 can include the first density 674 of windings per meter adjacent the first and second ends 610, 612 and the second density 676 of windings per meter between the first and second ends 610, 612. In one embodiment, the first density 674 of windings per meter is greater than the second density 676 of windings per meter.

In the embodiment of FIG. 6, the induction coil 602 and the capacitor structure 608 can be associated with a non-conductive elongate tube 678. In one embodiment, the non-conductive elongate tube 678 can be formed by an extrusion process. Alternatively, the non-conductive elongate tube 678 can be formed by a weaving or knitting process using one or more filaments, or multi-filament yarn, of the material as described herein.

Examples of suitable materials for use as the non-conductive elongate tube 678 include, but are not limited to, those described herein. In addition, the non-conductive elongate tube 678 can be formed, at least partially, of a biodegradable material, as are provided herein. As will be appreciated, the non-conductive elongate tube 678 may also be coated with one or more therapeutic agents, proteins, biomolecules, anticoagulant, anti-inflammatory, pro-endothelization compounds, among others, as described herein.

In one embodiment, examples of the non-conductive elongate tube can be found in co-pending U.S. patent application Ser. No. 11/207,304, entitle "Resonator for Medical Device" to Weber et al., which is hereby incorporated herein by reference in its entirety. This co-pending application provides embodiments of a structural support in the form of a tube that supports an induction coil and a capacitor for a resonator device. In various embodiments, the non-conductive elongate tube 678 can encase the induction coil 602 and/or the capacitor structure 608 of the resonator device 600. In an alterative embodiment, the non-conductive elongate tube 678 includes a peripheral surface on which the induction coil 602 is positioned.

Embodiments of the resonator device 600 can be used in association, or in conjunction, with a vascular stent or other medical device. For example, the resonator device can be provided over at least a part of the vascular stent. In another example, the resonator device 600 can be provided within at least a part of the vascular stent. The resonator device 600 in conjunction with the vascular stent can then operate in the presence of an electromagnetic field produced by an MRI system to reduce the artifacting (signal loss) in images obtained by an MRI system.

Figure 7:
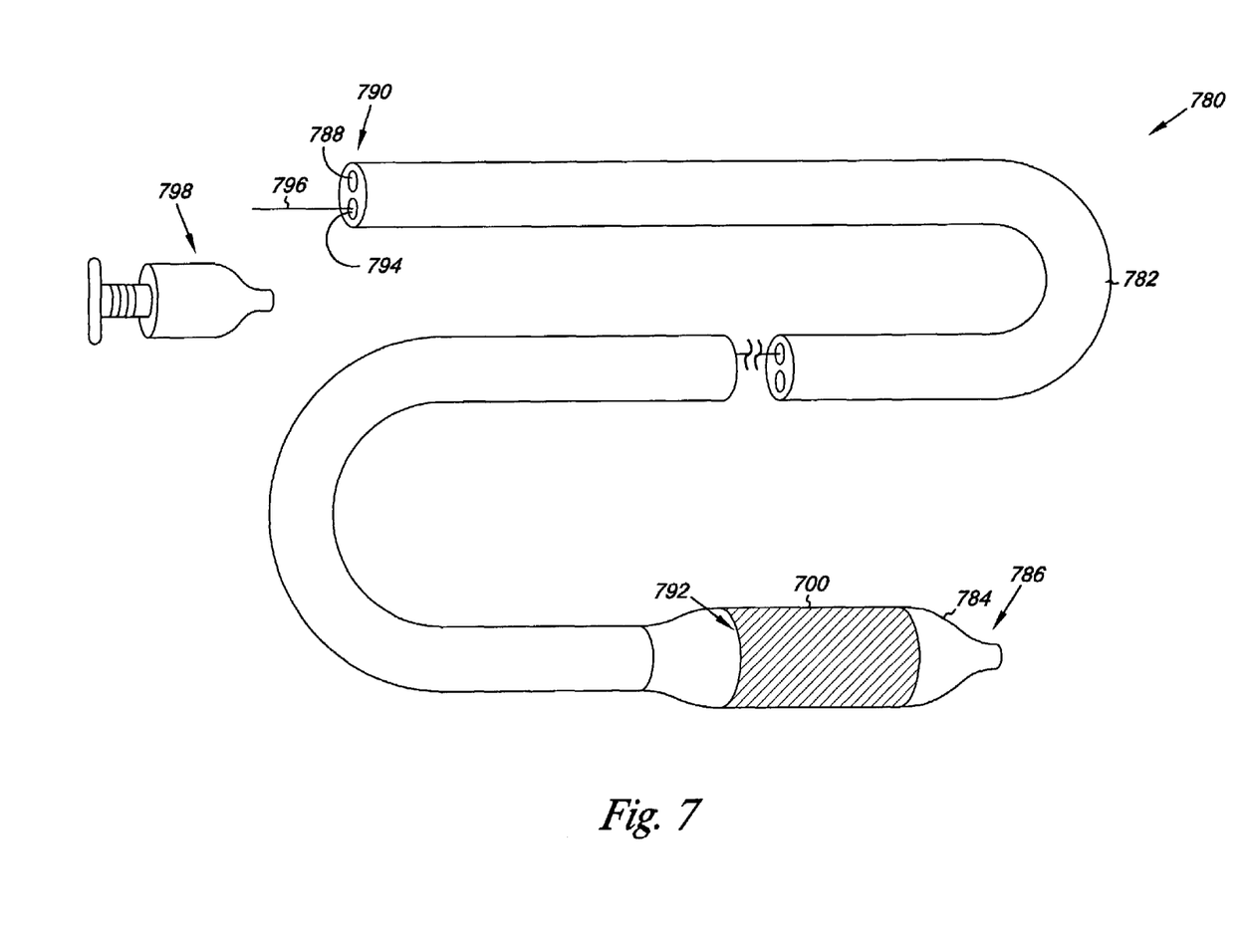
FIG. 7 illustrates an embodiment of a system including a resonator device according to the present invention.

FIG. 7 illustrates a system having a catheter 780 with an elongate body 782, an inflatable balloon 784 positioned adjacent a distal end 786, and a lumen 788 longitudinally extending in the elongate body 782 of the catheter 780 from the inflatable balloon 784 to a proximal end 790. In the present example, the inflatable balloon 784 can be at least partially positioned within the lumen 792 of the resonator device 700.

The catheter 780 can further include a guidewire lumen 794 to receive a guidewire 796. Guidewire 796 and guidewire lumen 794 assist in positioning the resonator device 700, as discussed herein, at a predetermined location within the body. Once in position, the inflatable balloon 784 can be inflated through the use of an inflation pump 798 that can releasably couple to the lumen 788. As the inflatable balloon 784 inflates, the resonator device 700 expands to the second diameter, as discussed herein, so as to position the resonator device 700 in the patient. As will be appreciated, lumen 788 and 794 can be eccentric, as illustrated, or concentric.

While the present invention has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the resonator device can be coated with a non-thrombogenic biocompatible material, as are known or will be known, one or more pharmaceuticals and/or biological compounds or molecules.

Embodiments and illustrations described herein can further be modified and/or added to according to co-pending U.S. patent application Ser. No. 09/779,204, entitled "Vascular Stent with Composite Structure for Magnetic Resonance Imaging Capabilities" [sic], which is incorporated herein by reference in its entirety.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A resonator device for a stent, comprising:
   an induction coil;
   a conductive member positioned adjacent the induction coil; and
   a dielectric layer between the induction coil and the conductive member to form a capacitor structure for the stent, the dielectric layer having a dielectric constant that changes in a predetermined fashion between the induction coil and the conductive member to allow for a uniform current distribution in the resonator device.

2. The resonator device of claim 1, where the conductive member is the stent having elongate members formed from an electrically conductive body, elongate members including an electrically conductive coating over the dielectric layer to provide the capacitor structure.

3. The resonator device of claim 2, where the induction coil includes a first end and a second end, where the first end couples to the electrically conductive body of the stent and the second end couples to the electrically conductive coating.

4. The resonator device of claim 3, where the dielectric layer includes two or more sections each having a dielectric constant that is different than the dielectric constant of other sections of the dielectric layer to change a capacitance value of the capacitor structure between the first end and the second end of the induction coil.

5. The resonator device of claim 4, where a value of the dielectric constant for the two or more sections increases between the first end and the second end of the induction coil to change the capacitance value of the capacitor structure between the first end and the second end of the induction coil.

6. The resonator device of claim 3, where the dielectric layer includes a thickness that increases along the stent between the first end and the second end of the induction coil to change a capacitance value of the capacitor structure.

7. The resonator device of claim 3, where the induction coil includes a first coil segment and a second coil segment, where the first coil segment includes the first end and the second coil segment includes the second end, and both the first and second coil segments are wound in a common direction.

8. The resonator device of claim 7, where the stent includes a first stent end and a second stent end, the first coil segment adjacent the first stent end and the second coil segment adjacent the second stent end.

9. A resonator device for implanting in a body, comprising:
   an induction coil having a first end and a second end, where the induction coil includes a first density of windings per meter adjacent the first and second ends and a second density of windings per meter between the first and second ends; and a capacitor in series with the induction coil, where the first density and the second density of windings per meter allow for a uniform current distribution in the resonator device.

10. The resonator device of claim 9, where the first density of windings per meter is greater than the second density of windings per meter.

11. The resonator device of claim 9, including a non-conductive elongate tube coupled to the induction coil and the capacitor.

12. The resonator device of claim 11, where the non-conductive elongate tube encases the induction coil.

13. The resonator device of claim 11, where the non-conductive elongate tube includes a peripheral surface on which the induction coil is positioned.

14. The resonator device of claim 13, where the induction coil is an electrically conducive thin film.

* * * * *